(12) United States Patent
Ghosh et al.

(10) Patent No.: US 10,526,257 B2
(45) Date of Patent: Jan. 7, 2020

(54) HEAVY PETROLEUM RESIDUE DERIVED IRON INCORPORATED SP² CARBON NANOGRANULES FOR IMPROVED SYNTHESIS OF LIGHT OLEFINS

(71) Applicant: COUNCIL OF SCIENTIFIC & INDUSTRIAL RESEARCH, New Delhi (IN)

(72) Inventors: Indrajit Kumar Ghosh, Dehradun (IN); Kumar Umesh, Dehradun (IN); Ankur Bordoloi, Dehradun (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 16/441,943

(22) Filed: Jun. 14, 2019

(65) Prior Publication Data

US 2019/0359540 A1     Nov. 28, 2019

Related U.S. Application Data

(62) Division of application No. 15/706,262, filed on Sep. 15, 2017, now Pat. No. 10,364,198.

(30) Foreign Application Priority Data

Nov. 2, 2016 (IN) ............... 201611037408

(51) Int. Cl.

| | | |
|---|---|---|
| *C07C 1/04* | (2006.01) | |
| *B01J 27/22* | (2006.01) | |
| *B01J 35/00* | (2006.01) | |
| *B01J 37/06* | (2006.01) | |
| *B01J 21/18* | (2006.01) | |
| *B01J 23/745* | (2006.01) | |
| *B01J 37/00* | (2006.01) | |
| *B01J 37/08* | (2006.01) | |
| *B01J 37/04* | (2006.01) | |

(52) U.S. Cl.
CPC ............... *C07C 1/044* (2013.01); *B01J 21/18* (2013.01); *B01J 23/745* (2013.01); *B01J 27/22* (2013.01); *B01J 35/002* (2013.01); *B01J 35/0006* (2013.01); *B01J 35/0013* (2013.01); *B01J 37/009* (2013.01); *B01J 37/04* (2013.01); *B01J 37/06* (2013.01); *B01J 37/084* (2013.01); *B01J 37/086* (2013.01); *C07C 1/0445* (2013.01); *C07C 2521/18* (2013.01); *C07C 2523/745* (2013.01); *Y02P 20/52* (2015.11)

(58) Field of Classification Search
CPC ......... C07C 1/044; C07C 11/04; C07C 11/06; B01J 35/002; B01J 23/745; B01J 37/084; B01J 33/06; B01J 35/0006; B01J 27/22; B01J 21/18; B01J 37/04; C10G 2/30; C10G 2/332

See application file for complete search history.

(56) References Cited

U.S. PATENT DOCUMENTS

2016/0107144 A1*   4/2016   Davidian ................ C07C 1/044
                                                                                         518/717

* cited by examiner

*Primary Examiner* — Jafar F Parsa
(74) *Attorney, Agent, or Firm* — K&L Gates LLP (57) ABSTRACT

Present invention relates to sp² carbon nanogranules with iron incorporated in it from heavy petroleum residue of a refinery and thereby utilizing the materials for improved synthesis of light olefins ($C_2$-$C_4$) from syngas in a single step Fischer Tropsch synthesis to lower olefins, (FTO). The efficient iron incorporated carbon nanogranules derived from low value heavy petroleum residue are very attractive as catalytic system for direct synthesis of light olefin ($C_2$-$C_4$) from syngas at CO conversion up to 30%.

10 Claims, 8 Drawing Sheets

HEAVY PETROLEUM RESIDUE DERIVED IRON INCORPORATED SP² CARBON NANOGRANULES FOR IMPROVED SYNTHESIS OF LIGHT OLEFINS

CROSS-REFERENCE TO A RELATED APPLICATION AND PRIORITY CLAIM

This application is a divisional application of U.S. patent application Ser. No. 15/706,262 filed Sep. 15, 2017 which claims the priority under at least 35 U.S.C. 119 to Indian Patent Application No. 201611037408 filed on 2 Nov. 2016, the entire contents of each of which are hereby incorporated by reference and relied upon.

FIELD OF THE INVENTION

The present invention provides a catalyst system derived from heavy petroleum/vacuum residues. The catalyst material is found to be very effective for direct synthesis of light olefin ($C_2$-$C_4$) from syngas with up to 30% CO conversion at reduced methanation and lower $CO_2$ formation.

BACKGROUND OF THE INVENTION

Vacuum residues, yellowish-green to dark brown liquid to semi-solid/solid consisting of polyaromatic hydrocarbons along with metals and heteroatoms, are mainly heavy petroleum residues derived from crude oil in refineries on vacuum distillation at a condition of temperature more than 550° C. Processing of such residues is associated with very high energy intensive operations due to rapid poisoning of catalysts and thereby is termed as waste from refinery. Such waste materials are mostly used in the construction, paving/road making, and roofing. These residues have high carbon to hydrogen ratio and as such can be utilized for the synthesis of many carbonaceous materials like carbon wool, carbon fiber, graphene, needle coke, pet coke etc.

On the other hand, light olefins ($C_2$-$C_4$) are highly valuable base stock for the production of n-number of daily useful petrochemical products. $C_2$-$C_4$ olefins are traditionally produced by thermal or catalytic cracking of naphtha or gas or vacuum gas oil. Market demand of $C_3$/$C_2$ olefin is in rise of 10-20% per annum while that for $C_4$/$C_2$ is of 30-40% per annum. The key is that markets have become supply-driven and the shortage in supply has made the olefin market is of great profitability. The necessity for alternative production routes for these major commodity chemicals via non-oil-based processes has driven research in past times during the oil crises. Currently, there is a renewed interest in producing lower olefins from alternative feed stocks such as coal, natural gas, or biomass, in view of high oil price fluctuations, environmental regulations, and strategies to gain independence from oil imports. With the increasing demand of these olefins and diminishing resources of crude petroleum and upcoming of gas and availability of carbonaceous resources (biomass, coal etc.), it is very important to develop processes based on these alternative feed stocks. Partial oxidation to syngas followed by Fischer-Tropsch synthesis seems to be one of the most promising routes in current century other than the methods of catalytic cracking of naphtha and dehydrogenation of alkanes. However, the selectivity of the desired products ruled by the Anderson-Schulz-Flory (ASF) model has always restricted the application of this method to an industrial setting.

The processes of converting synthesis gas into light olefins can be divided into two categories i.e., indirect and direct. The indirect routes involve selective synthesis of methanol or dimethyl ether or FT wax from syngas followed by their conversion to light olefins in second step, while the direct process involves a single step which is considered to be cost effective in terms of equipment and energy consumption.

Reference may be made to Patent CN102926031, wherein a cost effective process for the synthesis of carbon fibers from petroleum pitch/heavy aromatic hydrocarbon feed/asphalt has been described.

Reference may be made to Patent CN102728328, wherein asphalt has been used for automobile exhaust gas absorber along with porous material such as carbon fiber, carbon black, activated carbon.

Reference may be made to Patent CN10320450, wherein a method is reported for the preparation of high specific surface area activated carbon from carbon-rich residue obtained from high temperature coal tar or coal tar pitch. The carbon-rich residue mainly comprises quinoline insolubles and toluene insolubles removed from high temperature coal tar or coal tar pitch. The method includes subjecting the carbon-rich residue to pre-oxidation, grinding, dipping, drying, carbonization, activation and other processes so as to prepare an activated carbon material with a high specific surface area and a large pore volume that can be used in environmental protection, food processing, fine chemicals, medicines, super capacitors and other fields.

Reference may be made to Patent EP2920344, wherein description of a method of making a carbon fiber has been mentioned using reduced Tg lignin with a carbon residue selected from the group of coal based raw material, petroleum based raw material and combinations thereof. Reference may be made to Patent application No. US20030077450, wherein a method for synthesizing carbonaceous porous material having excellent mechanical strength has been disclosed from carbon residue at 500° C. or higher temperatures.

Reference may be made to PCT Application No. WO201623041, wherein a method for the synthesis of graphenes from crude oil derived asphaltene or any other polyaromatic hydrocarbon feed has been disclosed.

Reference may be made to Patent JP2006248817, wherein a manufacturing method for carbon nanotube from low-cost heavy hydrocarbons by chemical vapor deposition at 800-1300° C. has been disclosed.

Reference can be made to the Patent CN100341777C, wherein a practical method for the synthesis of carbon microballs/fullerenes from heavy oil residuals has been disclosed at high temperature of about 1100° C. The microballs are equally of spherical shape and free of byproducts such as carbon fibers and graphite flakes.

Reference may be made to U.S. Pat. No. 4,460,454, wherein a process for producing a pitch from heavy oil residue has been disclosed. The pitch could be used to produce carbon fibers having desirable characteristics.

Reference may be made to U.S. Pat. No. 4,604,185, wherein a process for the up-gradation of vacuum residues to fuel ranges distillates has been disclosed by using a feed consisting of vacuum residue and cracked residuum.

Reference may be made to Patent CN102698754B, wherein a preparation method of iron loaded carbon sphere has been disclosed and the catalytic activity of these materials for degradation of organic pollutants has been described.

Reference may be made to Patent CN102151575B, wherein a preparation method of iron loaded carbon nanotube has been disclosed and the materials have been reported to show activity for hydrogenation/dehydrogenation reactions in liquid phase.

Reference may be made to Patent CN105057001, wherein synthesis of an iron loaded carbon nanotube catalyst for the direct coal liquefaction hydrogenation reactions has been disclosed.

Reference may be made to the Patent WO201069133, wherein a promising catalyst composition has been described consisting of activated carbon with other support material and having one or more active metal sites e.g., Cu, Zn, V, Cr, Mn, Fe, Co, Ni, Zr, Mo, Sn and La etc. for the conversion of syngas ($H_2$:CO mostly greater than 2:1) to variety of chemicals like lower olefins up to the selectivity of 50%.

Reference may be made to Patent CN103394354B, wherein a preparation method for an iron loaded carbon sphere catalyst has been disclosed. The catalyst combinations shown to have syngas conversion activity with selectivity to methane 40 to 50% and lower olefins 35 to 40% at CO conversion of 50 to 80% at condition of temperature 340° C. and pressure 2.0 MPa at $H_2$:CO mole ratio 2:1. The catalyst with the effective composition disclosed has been reported to be prepared by using ion exchange resin beads which were placed in an aqueous solution of iron precursor salt with or without combination of auxiliary agents for a sufficient ion exchange, adsorption, precipitation and/or dipping so as to be uniformly supported and distributed on the surface of the ion exchange resin/or bore. The resin then undergoes extensive washing to remove excess catalyst effective component and/or auxiliary agents or their precursors followed by drying to remove moisture. The catalyst then obtained by thermal decomposition of the exchanged resins under inert atmosphere.

Reference may be made to Patent CN103406137B, wherein the invention is related to a nitrogen-doped carbon nanotube supported catalyst for Fischer-Tropsch synthesis of lower olefins. The catalyst has reported to show activity for CO conversion up to 15% with selectivity up to 47% and 55% for lower olefins in absence and presence of alkali promoters respectively while the selectivity of methane is up to 23% and 17%. But, the selectivity for $CO_2$ is 23% with alkali promoted catalyst while that without promoter is up to 18%.

Reference may be made to Patent CN102441384B, wherein a method for preparing iron loaded silica catalyst having high activity-stability carrier has been disclosed. The catalysts have shown to have activity in producing light olefins directly from syngas at condition of temperature up to 400° C., GHSV 1000 $h^{-1}$, pressure 2.0 MPa and $H_2$:CO (molar ratio) 1:1 in a high-pressure continuous fixed bed reactor with conversion of CO up to 80% and selectivity of light olefins ($C_2$-$C_4$) up to 50%. But no estimation on CO conversion to methane and $CO_2$ has been reported. Herein, we report for the first time, a practical approach for the synthesis of iron incorporated $sp^2$ carbon nanogranules from low value heavy petroleum residue/vacuum residue/polyaromatic hydrocarbons and the synthesized materials thereby provides an efficient catalyst system for direct synthesis of light olefin ($C_2$-$C_4$) from syngas with CO conversion up to 30% and lower olefin selectivity up to 50% at reduced methane and $CO_2$ formation.

OBJECTIVES OF THE INVENTION

The main object of the present invention is to provide iron incorporated $sp^2$ carbon materials from low value refinery residues and thereby utilizing the materials for improved production of lower olefins from syngas in a single step F-T route.

Another object of the present invention is to provide an improved process for converting syngas to high value light olefins ($C_2$-$C_4$) selectively with reduced formation of methane and carbon di-oxide.

Still another object of the present invention is to provide a promising approach to synthesize high value $sp^2$ carbon materials from low value refinery residue having polyaromatic hydrocarbons to create wealth.

Yet another object of the invention is to provide an efficient process for converting syngas to lower olefins in a single step F-T route rather than two step processes.

SUMMARY OF THE INVENTION

Accordingly, present invention provides an iron incorporated $sp^2$ carbon nanogranules Fe/CNG) catalyst wherein iron is in the range of 5 to 20 w/w % and iron is in Fe(0) form along with $Fe_3C$ phase.

In another embodiment of the present invention, Fe/CNG contains iron on the surface with traces of Fe(II) and Fe(III) phases.

In yet another embodiment of the present invention, the catalyst having characteristic 2θ values of 26.0, 43.5, 44.7±0.2 in the XRD.

Another aspect of the present invention is relates to a process for the preparation of catalyst and the said process comprising the steps of:
i. dissolving heavy petroleum residue in a solvent along with iron precursor to prepare a homogeneous solution;
ii. pumping the homogeneous solution as obtained in step (i) at flow range of 0.5 mL/min to 5 mL/min preferably 1 mL/min to 2 mL/min to a quartz reactor tube placed in the furnace and spraying the solution to the reactor tube in presence of nitrogen flow in the range of 100 to 300 mL/min preferably 200 to 250 mL/min for a time period of 10 minute to 60 minutes preferably 20 minutes to 40 minutes to obtain the carbon deposited on the tube surface;
iii. cooling the tube and collecting the carbon deposits from the surface as obtained in step (ii) of the reactor tube followed by washing with solvent to remove any unconverted residue;
iv. drying the carbon materials as obtained in step (iii) and calcining at temperature in the range of 400 to 700° C. preferably at 500 to 600° C. for a period in the range of 1 to 6 hours preferably 3 to 5 hours under nitrogen flow at 50 to 150 mL/min preferably 70 to 100 mL/min to obtain iron incorporated carbon nanogranules (Fe/CNG).

In yet another embodiment of the present invention, the heavy petroleum residues used is vacuum residue from refinery consisting of polyaromatic hydrocarbons (PAH).

In yet another embodiment of the present invention, the solvent used is an aromatic solvent selected from the group consisting of light naphtha, petroleum ether, benzene, toluene, xylene and ethylbenzene.

In yet another embodiment of the present invention, the iron precursor used is organometallic compound of iron preferably ferrocene.

In yet another preferred embodiment of the present invention, the iron precursor used is ferrocene.

In yet another embodiment of the present invention, the weight composition of the carbon source used is in the range of 5 to 20%.

In yet another embodiment of the present invention, the weight composition of vacuum residue used is in the range of 5 to 20% preferably 10 to 15%

In yet another embodiment of the present invention, the weight composition of the iron precursor used is in the range of 5 to 20%.

In yet another embodiment, present invention provides a process for the direct synthesis of lower olefins from syngas in a direct F-T route and the said process comprising the steps of:
i. reducing the catalyst under hydrogen or diluted hydrogen under pressure of atmosphere to 10 bar_g at temperature in the range of 350 to 500° C. preferably 400 to 450° C. for a time period in the range of 2 to 12 hours preferably 4 hours to 8 hours;
ii. cooling the catalyst bed followed by heating under the flow of syngas and nitrogen with $H_2$ to CO mole ratio is in the range of 0.5:1 to 2:1 preferably 1:1 to 1.5:1 at GHSV of 2000 to 5000 $mLh^{-1} g^{-1}$ preferably 2500 to 3500 $mLh^{-1} g^{-1}$ till the temperature reaches to 300 to 380° C. preferably 320 to 350° C. under atmospheric pressure;
iii.
iv. pressurizing the bed at 5 to 30 bar preferably 10 to 15 bars to obtain lower olefins.

In yet another embodiment of the present invention, CO conversion efficiency is up to 30% and selectivity of light olefins is up to 50%.

In yet another embodiment of the present invention, the light olefins from syngas obtained at lower rate of methanation of 15 to 17% and reduced conversion of CO to $CO_2$ at 12 to 15% with respect to the hydrocarbons.

In yet another embodiment of the present invention, the high temperature heating zone used for the synthesis of the carbon nanogranules is preferably a three zone furnace placed in vertical position with the center and lower zones are operated at temperature range of 800 to 1200° C. preferably 900 to 1000° C. with the upper zone is maintained at temperature range of 450 to 750° C. preferably 500 to 600° C.

In yet another embodiment of the present invention, the carbon materials synthesized from refinery residue consist of mainly graphitic $sp^2$ carbon.

In yet another embodiment of the present invention, the heavy petroleum residue has been subjected to high temperature treatment in presence of an inert solvent selected from the group consisting of light naphtha, petroleum ether, benzene, toluene, xylene and ethylbenzene preferably toluene under atmosphere of nitrogen.

In yet another embodiment of the present invention, an iron precursor is used in homogeneous phase with petroleum residue in presence of an aromatic solvent.

In yet another embodiment of the present invention, the carbon materials from vacuum residues are pretreated for the reduction of surface iron phases prior to F-T reaction.

In yet another embodiment of the present invention, prior to the heat treatment to synthesize Fe/CNGs, the heavy petroleum residue is dissolved in an aromatic solvent along with a precursor of iron.

In yet another embodiment of the present invention, the solvent used for preparing homogeneous mixture of carbon source and iron precursor to a suitable composition is selected from light naphtha, petroleum ether, benzene, toluene, xylene and ethylbenzene.

In yet another embodiment of the present invention, the iron precursor used in homogeneous mixture with carbon source belongs to the class of organometallic compound of iron preferably soluble in aromatic solvent.

In yet another embodiment of the present invention, the iron precursor used for the synthesis of Fe/CNGs along with residues belongs to the class of organometallic complex of iron preferably ferrocene.

In yet another embodiment of the present invention, the carbon nanogranules show activity for direct synthesis of lower olefins at CO conversion up to 30% at selectivity of light olefins up to 50%.

In yet another embodiment of the present invention, the light olefins from syngas obtained at comparatively lower rate of methanation of 15 to 17% and reduced conversion of CO to $CO_2$ at 12 to 15% with respect to the hydrocarbons.

In yet another embodiment of the present invention, the olefins can further be utilized for the production of n-number of useful petrochemicals the demand of which is increasing at the rate of 4 to 7% per annum.

BRIEF DESCRIPTION OF THE DRAWING

FIG. 1 represents the synthesis scheme of Fe/CNGs from heavy petroleum residues wherein 1. Homogeneous solution of CNG precursor and organometallic iron precursor in a solvent, 2. High pressure nitrogen (UHP grade) cylinder, 3. Reciprocating pump, 4. Double stage gas regulator, 5. Mass flow controller, 6. Check valve, 7. Sprayer, 8. Quartz reactor tube, 9. Three zone tubular split furnace, 10. Flask for collecting Fe/CNGs, 11. Stand for holding the furnace, 12. Gas stream from CNG collector.

FIG. 2 is schematic representation of high pressure continuous flow fixed bed reactor setup for carrying out performance evaluation of Fe/CNGs for conversion of syngas to light olefins in a direct F-T route; wherein 1: Cylinder pressure regulator, 2: Needle valve, 3: Pressure gauge, 4: Mass flow controller (MFC), 5: Check Valve, 6: Gas mixer, 7: Gas preheater, 8: Pressure safety relief valve, 9: Reactor tube, 10: Single zone tubular split furnace, 11: Heating zone of furnace, 12: Temperature sensor for catalyst bed inside the reactor, 13: Temperature sensors for the skin of the reactor tube, DTC: Digital Temperature Controller, 14: Condenser separator, 15: Back Pressure Regulator (BPR), 16: Three way valve, 17: Bubble gas flow meter, 18: Gas stream for GC, RGA: Refinery Gas Analyzer.

FIG. 7 represents the time on stream activity profile of the Fe/CNG catalysts for the selective synthesis of lower olefins for a period of 25 hours.

FIG. 8 represents the Anderson-Schulz-Flory (ASF) model for the calculation of chain growth probability (α) based on the distribution of hydrocarbons in the invented catalyst system for the single step conversion of syngas to light olefins.

DETAILED DESCRIPTION OF THE INVENTION

The present invention provides a process for the synthesis of $sp^2$ carbon nanogranules with iron incorporated in it from low value refinery residue preferably vacuum residue and thereof utilization of the carbon nanogranules as efficient catalyst system for improved synthesis of lower olefins ($C_2$-$C_4$) from syngas in direct single step Fischer Tropsch process (FTO). The designed materials catalyze to synthesize light olefins at a lower methanation rate with reduced $CO_2$ formation in comparison to the other reported costlier carbon catalytic materials. The steps comprises dissolution of heavy petroleum residue in an aromatic solvent along with a desirable amount of iron precursor to prepare a homogeneous solution, spraying the solution with the aid of nitrogen to a quartz tube reactor operated at high temperature at atmospheric pressure, scratching out the carbon deposits from the surface of the reactor tube and washing with aromatic solvent to remove any unconverted residue, drying the carbon materials and calcining under nitrogen to obtain desirable iron incorporated carbon nanogranules (Fe/CNG), treating the Fe/CNGs under hydrogen or diluted hydrogen atmosphere and finally carrying out hydrogenation of carbon monoxide (CO) in presence of Fe/CNGs as catalyst system.

The process of the present invention involves a practical approach for the synthesis of $sp^2$ carbon nanogranules with iron content from low value heavy petroleum residue of refinery and thereby utilizing the carbon materials for efficient synthesis of lower olefins from syngas by direct F-T process. In synthesizing the carbon nanogranules, firstly heavy petroleum residue preferably vacuum residue to a weight composition of 5 to 20% preferably 10 to 15% is dissolved in an aromatic solvent preferably toluene along with an organometallic compound of iron preferably ferrocene as iron precursor to weight composition of 5 to 20% to prepare a homogeneous solution. The solution is then pumped at the flow range of 0.5 mL/min to 5 mL/min preferably 1 mL/min to 2 mL/min with the aid of a reciprocating pump (flow range: 0.01-10 mL/min) to a heated quartz reactor tube (Diameter: 60 mm, Length: 1200 mm) kept through a three zone tubular split furnace with heating capacity up to 1200° C. having adjustable diameter and length of 900 mm. The upper zone of the furnace is maintained at 450 to 750° C. preferably 500 to 600° C. while the middle and the lower zones are at 800 to 1200° C. preferably 900 to 1000° C. The solution is sprayed to the reactor tube with the aid of nitrogen gas flow in the range of 100 to 300 mL/min preferably 200 to 250 mL/min for a time period of 10 minutes to 60 minutes preferably 20 minutes to 40 minutes. Then the tube is cooled down to room temperature under nitrogen flow and the carbon deposits are collected from the reactor tube. The carbon materials are then purified by washing with toluene followed by drying in oven at 80 to 110° C. Finally the iron incorporated carbon nanogranules are synthesized by calcining the purified carbon materials under the flow of nitrogen at 50 to 150 mL/min preferably 70 to 100 mL/min at the condition of temperature in the range of 400 to 700° C. preferably at 500 to 600° C. for 1 to 6 hours preferably 3 to 5 hours. The same experiment is repeated with the aromatic solvent used for preparing the homogeneous solution in blank to find the distinction of yield amount in comparison to heavy hydrocarbons.

For the measurements of catalytic activity, the Fe/CNG samples are crushed, pelletized, sieved (20 to 30 mesh) and diluted with SiC granules. About 2.0 g of each catalyst after dilution are loaded in the reactor in each of the experiments. The catalyst bed is initially flushed with nitrogen and heated up to temperature range of 350 to 500° C. preferably 400 to 450° C. at heating rate of 1 to 10° C./min preferably 2 to 5° C. and kept for a time period of 2 to 12 hours preferably 4 to 8 hours under hydrogen atmosphere or diluted hydrogen atmosphere with nitrogen with flow of nitrogen at 60 to 65 mL/min and hydrogen 20 to 25 mL/min to reduce the catalyst under condition of pressure of atmospheric to 10 bar_g preferably atmospheric to 5 bar_g. After the reduction, the bed is cooled down and again kept on heating under the flow of syngas and nitrogen with $H_2$:CO mole ratio at 0.5:1 to 2:1 preferably 1:1 to 1.5:1 at GHSV of 2000 to 5000 mLh$^{-1}$ g$^{-1}$ preferably 2500 to 3500 mLh$^{-1}$ g$^{-1}$ till the temperature of the bed reaches to 300 to 380° C. preferably 320 to 350° C. under atmospheric pressure. Once the temperature is attained, the bed is pressurized by turning the knob of BPR to the value of gauge at 5 to 30 bar preferably 10 to 15 bars. The Fe/CNGs were tested for a time of stream of 25 hours to determine the activity towards selective synthesis of light olefins in a single step.

To check the activity of the Fe/CNGs following were calculated:

CO Conversion:

$$X_{CO}(\%) = \frac{\text{mole of CO in} - \text{mole of CO out}}{\text{mole of CO in}} \times 100$$

Selectivity for Hydrocarbon y:

$$S_y(\%) = \frac{\text{mole of CO converted to } y}{\text{mole of CO reacted*}} \times 100$$

[* excluding conversion to $CO_2$ and $H_2O$]

Selectivity for $CO_2$:

$$S_{CO_2}(\%) = \frac{\text{mole of CO converted to } CO_2}{\text{mole of CO converted to hydrocarbon}} \times 100$$

α Value for ASF Model:

The chain growth probability (a) factor for the present catalyst system is evaluated as per FIG. 8 to identify the deviation of component distribution in hydrocarbon product from the conventional ASF model.

Heavy petroleum refinery residue preferably vacuum residue is utilized. However, the scope of invention is not limited to these streams only and other feeds containing at least polyaromatic hydrocarbons may be used.

FIG. 1 represents the synthesis scheme of Fe/CNGs from heavy petroleum residues wherein 1. Homogeneous solution of CNG precursor and organometallic iron precursor in a solvent, 2. High pressure nitrogen (UHP grade) cylinder, 3. Reciprocating pump, 4. Double stage gas regulator, 5. Mass flow controller, 6. Check valve, 7. Sprayer, 8. Quartz reactor tube, 9. Three zone tubular split furnace, 10. Flask for collecting Fe/CNGs, 11. Stand for holding the furnace, 12. Gas stream from CNG collector.

Prior to synthesis, the reactor tube 8 is initially purged with nitrogen gas (99.999%) from cylinder 2 and heated by a three zone split tubular furnace 9 kept upright with the help of a stand 11 at the desired temperature under an inert atmosphere of nitrogen. A homogeneous solution 1 comprising of heavy petroleum residue or vacuum residue or polyaromatic hydrocarbon or in suitable combination along with organometallic iron precursor is pumped by a reciprocating pump 3 and sprayed by sprayer 7 to the quartz tube reactor 8 placed at the heated zone of furnace with the aid of controlled flow of nitrogen by mass flow controller 5. The pressure of nitrogen in upstream of mass flow controller (MFC) is controlled by the double stage cylinder regulator 4 while that in downstream by the check valve 6 ensuring forward flow of nitrogen gas up to the outlet 12. The reactor tube is later on allowed to cool down under the constant flow of nitrogen. The carbon layers from the reactor tube are then separated and collected in the flask 10 and washed with an aromatic solvent to purify. Finally, the purified carbon materials are calcined under the flow of nitrogen to obtain Fe/CNGs.

FIG. 2 is schematic representation of high pressure continuous flow fixed bed reactor setup for carrying out performance evaluation of Fe/CNGs for conversion of syngas to light olefins in a direct F-T route; wherein 1: Cylinder pressure regulator, 2: Needle valve, 3: Pressure gauge, 4: Mass flow controller (MFC), 5: Check Valve, 6: Gas mixer, 7: Gas preheater, 8: Pressure safety relief valve, 9: Reactor tube, 10: Single zone tubular split furnace, 11: Heating zone of furnace, 12: Temperature sensor for catalyst bed inside the reactor, 13: Temperature sensors for the skin of the reactor tube, DTC: Digital Temperature Controller, 14: Condenser separator, 15: Back Pressure Regulator (BPR), 16: Three way valve, 17: Bubble gas flow meter, 18: Gas stream for GC, RGA: Refinery Gas Analyzer.

All gas lines connected to the reactor tube 9 were made of ¼" stainless steel tubing. Three mass flow controllers (Brooks) 4 equipped with a four-channel control panel are used to adjust the flow rate of the inlet gases ($CO+N_2$, $H_2$ and $N_2$ with purity of 99.99%). The gases with proper flow rate at first undergo intensive mixing in a mixer 6. The mixed gas then passes into the preheater 7 followed by reactor tube 9 which is placed inside a single zone split tubular furnace 10 capable of producing temperature up to 800° C. and is controlled by a digital temperature controller (DTC). The reactor tube is made of stainless steel having internal diameter of 20 mm capable of sustaining pressure up to 80 bar at temperature 800° C. The reactor tube consists of three zone 11: preheating zone which is filled with SiC granules (1-2 mm), zone temperature up to 250 to 300° C.; catalysts bed zone which is situated almost in the middle of the reactor, contains mixture of catalyst particles (20 to 30 mesh) mixed with SiC granules (20 to 30 mesh) to a volume ratio of 1:(3 to 5), zone temperature 300 to 450° C.; product dispersion zone which is filled with porcelain beads of internal diameter of 1 mm and outer diameter of 2.5 mm, zone temperature up to 250° C. The product stream from the reactor then moves downward to the condenser separator 14 where separation of gas and liquid takes place. The liquid product from the separator bottom is then collected through a pressure trap system while the gas from the separator comes out through a BPR 15. The BPR is capable to maintain pressure inside the reactor to a desired value up to 100 bar at the reactor operating condition. The gas stream post BPR is taken through a three way ball valve 16 either to a bubble flowmeter 17 for calculating flow or to a gas chromatography (GC) 18 [Agilent, 7890B, equipped with two FID for hydrocarbons $C_1$-$C_{12}$, HP-$Al_2O_3$/KCL column (25 m×0.320 mm; 5 μm) & CP-SIL 2CB column (25 m×0.320 mm; 1.2 μm) and one TCD for the permanent gases $H_2$, $CO_2$, $N_2$, CO, Hayesep Q column (6 ft×⅛×2 mm)] for identifying and quantifying the composition.

Figure 3:
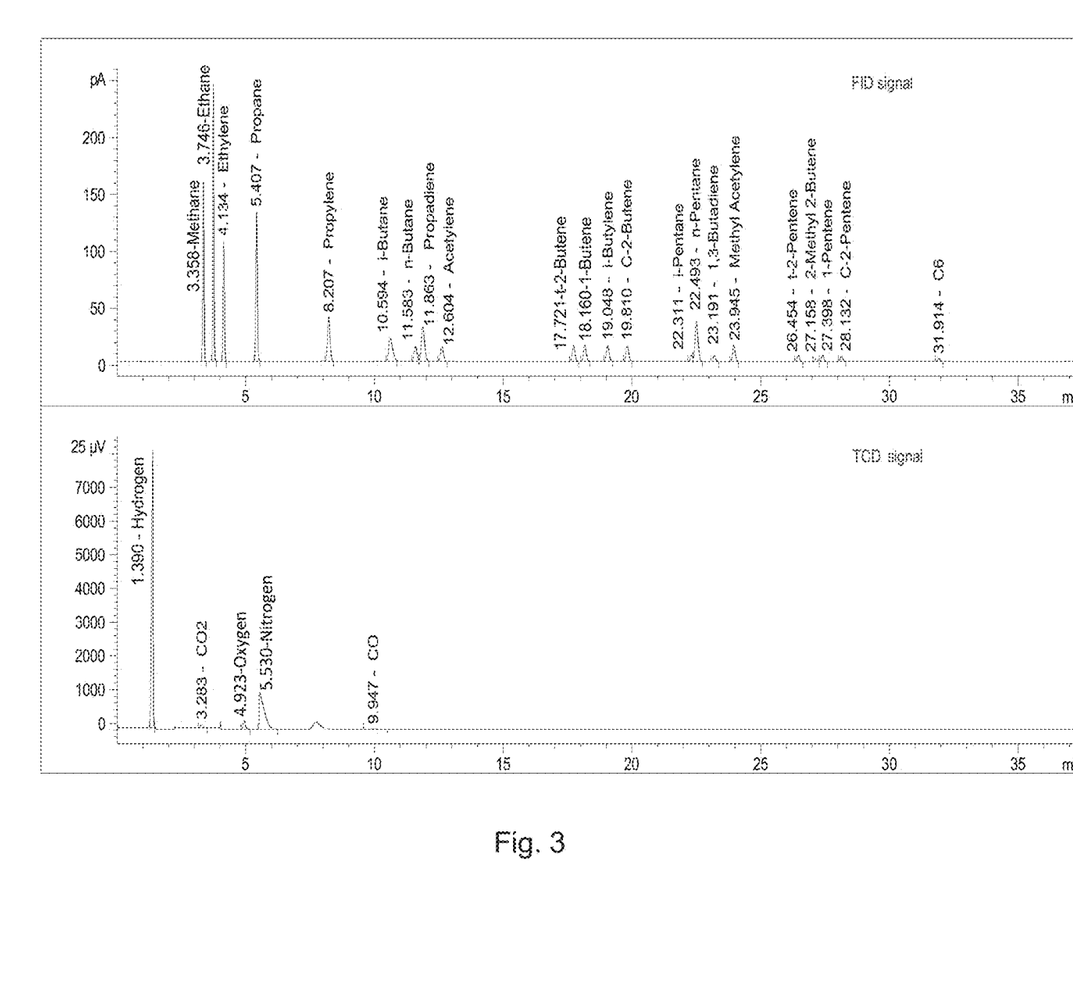
FIG. 3 represents the chromatography of the hydrocarbons ($C_1$-$C_6$) and permanent gases with their respective retention times (RT, min in x-axis) required to find out the composition of both the feed and product streams in the conversion of syngas in presence of Fe/CNGs as catalysts.

FIG. 3 represents the chromatography of the hydrocarbons ($C_1$-$C_6$) and permanent gases with their respective retention times (RT, min in x-axis) required to find out the composition of both the feed and product streams in the conversion of syngas in presence of Fe/CNGs as catalysts.

Figure 4:
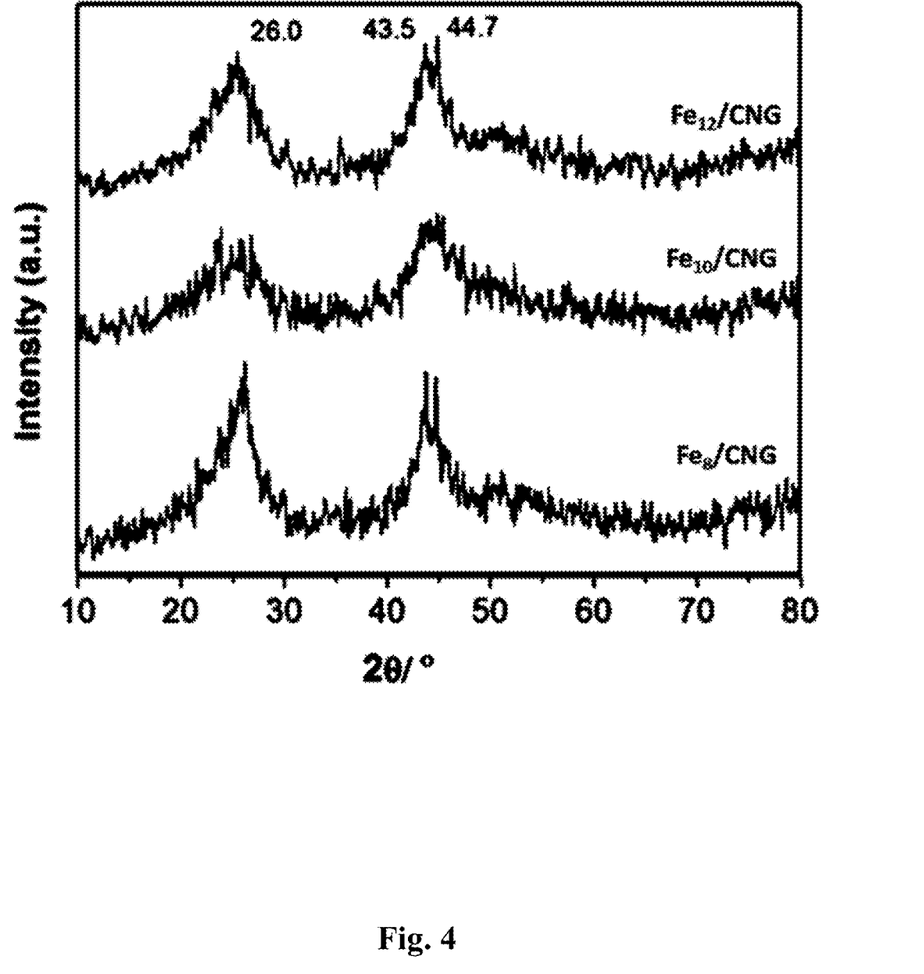
FIG. 4 shows the X-ray diffraction patterns of Fe/CNGs e.g., $Fe_8$/CNG, $Fe_{10}$/CNG and $Fe_{12}$/CNG synthesized from varying composition of iron precursor in the homogeneous solution.

FIG. 4 shows the X-ray diffraction patterns of Fe/CNGs e.g., $Fe_8$/CNG, $Fe_{10}$/CNG and $Fe_{12}$/CNG synthesized from varying composition of iron precursor in the homogeneous solution. X-ray diffraction (XRD) patterns were obtained on a Bruker D8 advance X-ray diffractometer using monochromatic CuKα (λ=1.5418 Å) radiation in 2θ range from 10 to 80° with a step size 0.04°.

Major peaks at 26°, 43.5° (2θ) corresponding to the reflection of 002 and 101 hkl planes, represent the graphite form of carbon with hexagonal phases (JCPDS card No. 75-1621), whereas the broad peaks with sample $Fe_{10}$/CNG possibly because of the presence of carbon in amorphous form. The peaks at 44.7° in all the Fe/CNG samples confirm the presence of iron [Fe(0)]. The presence of iron in the Fe/CNG samples were also confirmed by ICP-AES and calcining the samples at 700 to 1000° C. preferably at 800 to 950° C. under air. The CNG samples are therefore named as per the iron content in it, e.g., $Fe_{10}$/CNG represents the carbon nanogranules with iron content of 10% by weight. There are no characteristic peaks of iron oxide [Fe(II) or Fe(III)] appeared in XRD pattern of all the synthesized CNGs. This confirms the prepared Fe/CNG catalysts unanimously have [Fe(0)] in bulk phase.

Figure 5A:
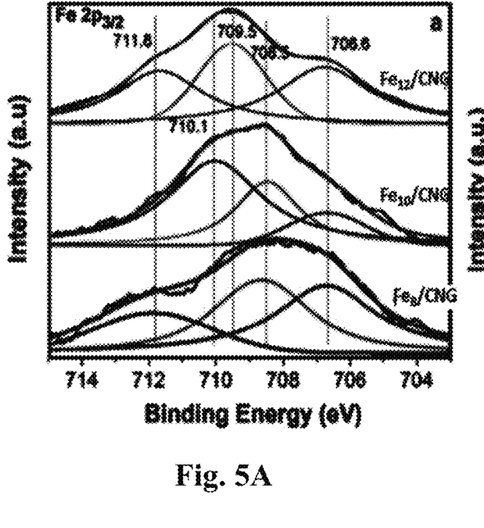
FIG. 5A represents the X-ray Photoelectron spectroscopy (XPS) spectra of surfaces of $Fe_8$/CNG, $Fe_{10}$/CNG and $Fe_{12}$/CNG in Fe2p region.
Figure 5B:
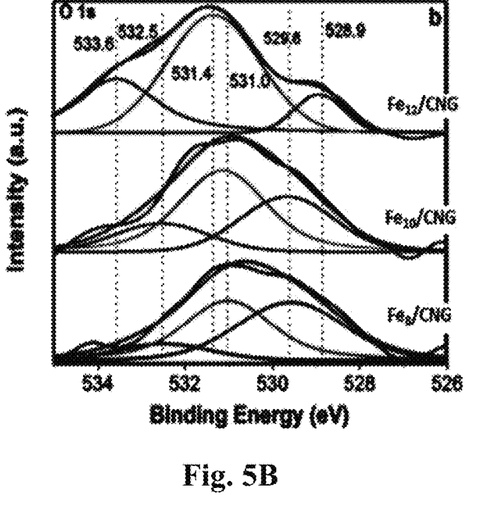
FIG. 5B represents XPS spectra of surfaces of $Fe_8$/CNG, $Fe_{10}$/CNG and $Fe_{12}$/CNG in O1s region.
Figure 5C:
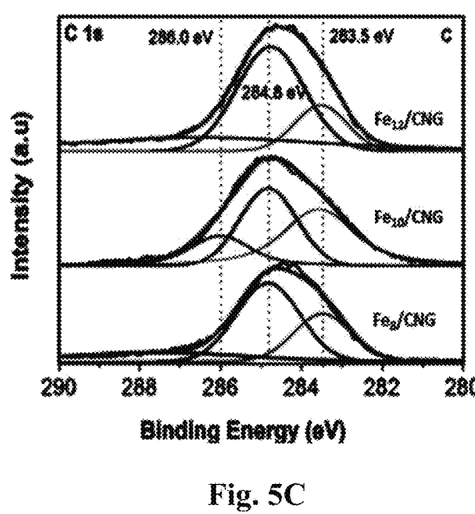
FIG. 5C represents XPS spectra of surfaces of $Fe_8$/CNG, $Fe_{10}$/CNG and $Fe_{12}$/CNG in C1s region.

FIG. 5A represents the XPS spectra of surfaces of $Fe_8$/CNG, $Fe_{10}$/CNG and $Fe_{12}$/CNG in Fe2p region. X-ray Photoelectron spectroscopy (XPS) analyses of the materials were carried out on model: SN-10001, Prevac Poland, with a VG Scienta-R3000 hemispherical energy analyser. The Fe 2p3/2 binding energy peak at 706.6 eV in all the samples prove the presence of [Fe(0)] which is in concomitant with XRD analyses. Nevertheless, the peak at 708.5 eV in $Fe_8$/CNG and $Fe_{10}$/CNG belongs to surface $Fe_2O_3$ and peak at 709.5 eV in Fe/CNG pellets belongs to surface FeO, while peak at 710.1 eV in $Fe_{10}$/CNG belongs to Fe(III) oxides and peak at 711.8 eV in $Fe_{12}$/CNG belongs to surface iron oxo-hydroxo (FeOOH) species due to air exposure. The CNG samples are reduced in-situ prior to the reaction. The XPS of O1s were fitted for the three samples as shown in FIG. 5B. The peak at 529.6 eV corresponds to the binding energy of $O^{2-}$. The other peaks at 531.4 eV and 532.5 eV could be assigned as O1s in [$OH^-$]. Here the oxygen species present in the samples are similar to the oxygen species present on iron. In the C1s spectrum of the three samples as shown in FIG. 5C, the peak at 284.8 eV confirms $sp^2$ hybridization of graphitic carbon, the deconvoluted peak at 283.5 eV is correspond to surface $Fe_3C$ species and 286.0 eV corresponds to C—O species.

$H_2$-Temperature-programmed reduction ($H_2$-TPR) of the carbon nanogranules were performed using a Chemisorption analyser, Autochem 2920 (Micromeritics, USA) equipped with a conventional atmospheric quartz flow reactor (5 mm ID). Prior to the reduction studies, pre-treatment of samples (70 mg) inside the reactor were carried out at temperature of 350° C. under flow of helium (99.995%) at 50 mL/min for 3 hours. The reactor was then cooled down to room temperature under the flow of helium and the TPR studies were carried out by heating the reactor from 50° C. to 1000° C. at a rate of 10° C./min under the flow of 10% $H_2$/Ar (on mole basis) at 30 mL/min. the TPR profiles were recorded by using the response of the thermal conductivity detector (TCD) of the effluent gas.

Figure 5D:
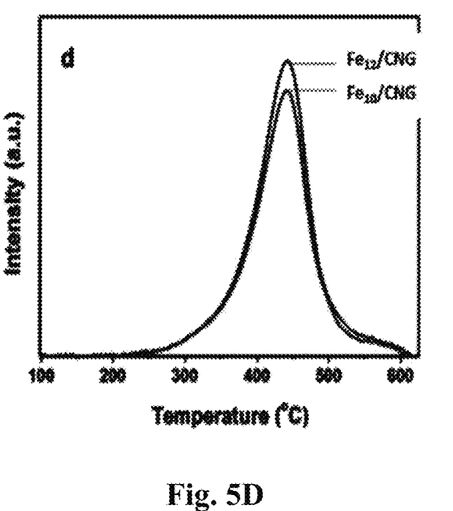
FIG. 5D represents the $H_2$-TPR profile of the Fe/CNGs.

The $H_2$-TPR profile of the Fe/CNGs according to the FIG. 5D, also confirms the requirement of Fe/CNGs to reduce prior to the reaction. The single broad peak area at 435-440° C. in the TPR profiles corresponding to the reduction of $Fe_2O_3$ phase to Fe(0). The shifting of the peak in comparison to the pure Fe(0) evidences the strong metal support interaction in prepared catalyst system.

FIGS. 6A, 6B, 6C, 6D, 6E and 6F represent the structure and morphology of synthesized Fe/CNGs analyzed by SEM and TEM. Morphological information of the catalyst samples were obtained by FEI Quanta 200F scanning electron microscope (SEM) system equipped with energy-dispersive X-ray (EDX) spectroscopy. Transmission electron microscopic (TEM) analyses were performed on FEI model no. Technai G220 S-TWIN instrument.

Figure 6A:
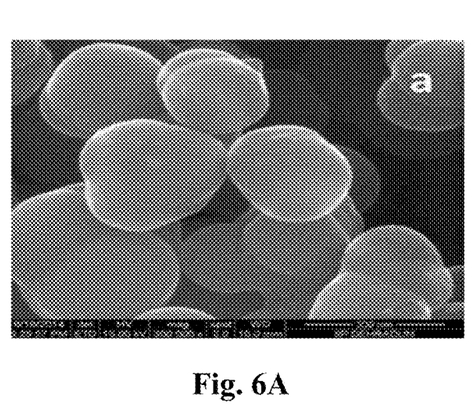
FIGS. 6A, 6B and 6C represent the SEM image of $Fe_8$/CNG, $Fe_{10}$/CNG and $Fe_{12}$/CNG particles respectively.
Figure 6B:
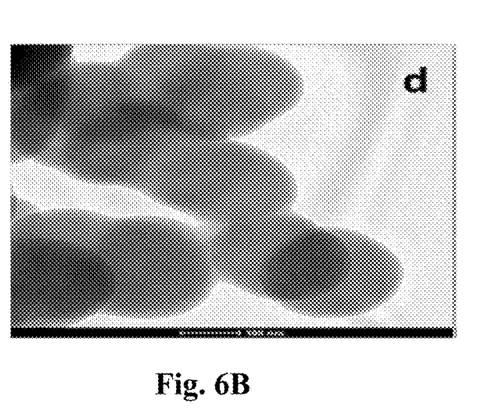
Figure 6C:
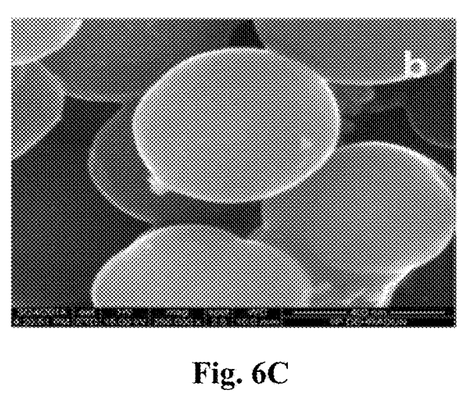
Figure 6D:
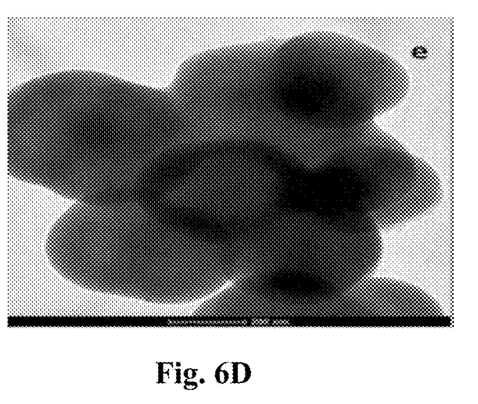
FIGS. 6D, 6E and 6F represent the TEM image of $Fe_8$/CNG, $Fe_{10}$/CNG and $Fe_{12}$/CNG particles respectively.
Figure 6E:
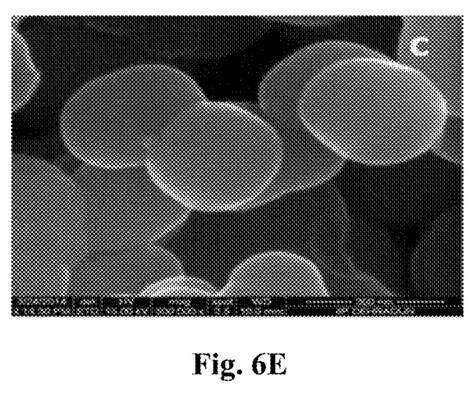
Figure 6F:
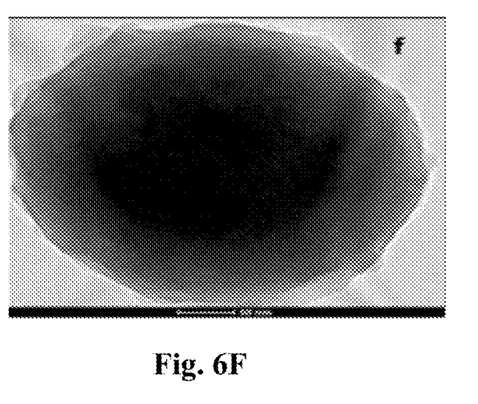

SEM and TEM image of Fe/CNGs prepared show spherical granular shape of the particles. According to the images, the $Fe_8$/CNG and $Fe_{12}$/CNG particles have diameter less than 300 nm (FIGS. 6a & 6c) while $Fe_{10}$/CNG has diameter more than 400 nm (FIG. 6b). The TEM images of $Fe_{10}$/CNG indicate the particle size of less than 50 nm (FIG. 6 d-f).

FIG. 7 represents the time on stream activity profile of the Fe/CNG catalysts for the selective synthesis of lower olefins for a period of 25 hours. The figure shows that Fe/CNGs are attractive catalyst system providing a stable activity pattern for conversion of syngas to lower olefins.

FIG. 8 represents the Anderson-Schulz-Flory (ASF) model for the calculation of chain growth probability (a) based on the distribution of hydrocarbons in the invented catalyst system for the single step conversion of syngas to light olefins. The a value enables to predict the deviation from the conventional distribution of product components in F-T synthesis that is required to develop process for short chain olefins.

EXAMPLES

The following examples are given by way of illustration of the present invention and therefore should not be construed to limit the scope of the present invention.

Example 1

A homogeneous solution containing 10% Vacuum residue (VR-550+) and 10% ferrocene dissolved in toluene was pumped at flow rate of 1 mL/min and sprayed through the heated zone of furnace with the aid of flow of nitrogen at 200 mL/min for 30 minutes. After that, the reactor tube was allowed to cool down under the constant flow of nitrogen. The carbon layers from the reactor tube were then separated and washed with toluene to purify. Finally, the purified carbon materials were calcined at 600° C. for 3 hrs under the flow of nitrogen at 80-90 mL/min to obtain Fe/CNGs. The Fe/CNG is named as $Fe_8$/CNG as it contain 8% of iron by weight as per ICP-AES analysis. The XRD, XPS and SEM images of the $Fe_8$/CNG are represented in the FIG. 4, FIG. 5 and FIG. 6 respectively.

Example 2

A homogeneous solution containing 10% Vacuum residue (VR-550+) and 15% ferrocene dissolved in toluene was used for the synthesis of Fe/CNG as given in example 1 and the resulted Fe/CNG is termed as $Fe_{10}$/CNG consisting of 10% iron by weight. The XRD, XPS and SEM & TEM images of the $Fe_{10}$/CNG are represented in the FIG. 4, FIG. 5 and FIG. 6 respectively.

Example 3

A homogeneous solution containing 10% Vacuum residue (VR-550+) and 20% ferrocene dissolved in toluene was used for the synthesis of Fe/CNG as given in example 1 and the resulted Fe/CNG is termed as $Fe_{12}$/CNG consisting of 12% iron by weight. The XRD, XPS and SEM images of the $Fe_{12}$/CNG are represented in the FIG. 4, FIG. 5 and FIG. 6 respectively.

Example 4

The synthesized Fe/CNGs in examples 1-3 were crushed and pelletized to 20-30 mesh size and loaded in the fixed bed reactor setup for analyzing the activities for synthesis of light olefin from syngas. The catalyst bed was initially treated at the temperature of 400° C. for 8 hours under continuous flow of hydrogen of 20 mL/min and nitrogen 65 mL/min in order to reduce the Fe/CNGs. Hydrogenation of carbon monoxide was then conducted over the catalysts bed at temperature of 340° C., pressure of 15 bar_g, GHSV of 3000 mL $h^{-1}$ $g^{-1}$ and $H_2$:CO mole ratio of 1.15:1 for 25 hours of time on stream. Following table represents the performance of the Fe/CNGs in the hydrogenation of CO in the synthesis of lower olefins in a direct F-T route.

TABLE 1

Experimental data for single step conversion of syngas to hydrocarbons using catalysts described in examples 1-3

| Catalyst | $X_{co}$ | $S_{CO_2}$ | $S_{CH_4}$ | $S_{C2-C4}^=$ | $S_{C2-C4}^{paraffin}$ | $S_{C5+}$ | α |
|---|---|---|---|---|---|---|---|
| $Fe_8$/CNG | 13.5 | 14.60 | 14.99 | 51.88 | 9.76 | 23.37 | 0.5 |
| $Fe_{10}$/CNG | 24.3 | 12.73 | 17.02 | 49.12 | 12.48 | 21.39 | 0.53 |

($X_{co}$=conversion of CO in the hydrogenation reaction; $S_{CO_2}$=selectivity of CO conversion to $CO_2$ in comparison to the hydrocarbons; $S_{CH_4}$, $S_{C2-C4}^=$, $S_{C2-C4}^{paraffin}$, $S_{C5+}$=selectivity of formation of methane, $C_2$-$C_4$ olefins, $C_2$-$C_4$ paraffins and hydrocarbons heavier than $C_4$ respectively from CO upon hydrogenation; α=ASF factor in the formation of hydrocarbons)

The time on stream analyses of the Fe/CNGs have been shown in the FIG. 7 representing stable activity pattern for a time of run of 25 hours.

Example 5

As in example 4, the hydrogenation of CO is carried out over $Fe_{10}$/CNG catalyst at condition of pressure of 20 bar_g.

TABLE 2

Hydrogenation of CO over $Fe_{10}$/CNG catalyst at 20 bar_g

| Catalyst | $X_{co}$ | $S_{CO_2}$ | $S_{CH_4}$ | $S_{C2-C4}^=$ | $S_{C2-C4}^{paraffin}$ | $S_{C5+}$ | α |
|---|---|---|---|---|---|---|---|
| $Fe_{10}$/CNG | 19.9 | 12.10 | 25.41 | 45.40 | 10.74 | 18.45 | 0.5 |

Example 6

As depicted in example 4, the direct F-T reaction is carried out over $Fe_{10}$/CNG catalyst at condition of temperature of 320° C.

TABLE 3

Hydrogenation of CO over $Fe_{10}$/CNG catalyst at 320° C.

| Catalyst | $X_{co}$ | $S_{CO_2}$ | $S_{CH_4}$ | $S_{C2-C4}^-$ | $S_{C2-C4}^{paraffin}$ | $S_{C5+}$ | α |
|---|---|---|---|---|---|---|---|
| $Fe_{10}$/CNG | 21.2 | 11.91 | 17.60 | 47.23 | 13.43 | 21.73 | 0.52 |

Advantages of the Invention

The present invention provides an efficient pathway of utilization of low value refinery residue for the synthesis of high value olefins by;
a) synthesizing $sp^2$ carbon nanogranules with iron incorporated in it from heavy petroleum residue having polyaromatic hydrocarbon content
b) conducting direct F-T synthesis of light olefins in fixed bed reactor over the Fe/CNGs as catalyst system The main advantages of the present invention are:

Synthesis of lower olefins utilizing the iron incorporated carbon nanogranules derived from low cost heavy petroleum residues in a direct F-T route with selectivity of up to 50% at CO conversion of up to 30%.

Reduced methanation and $CO_2$ formation in the selective synthesis of light olefins in a single step hydrogenation of carbon monoxide.

Provides an attractive pathway for creating wealth from waste refinery residues

We claim:

1. A process for the direct synthesis of lower olefins from syngas using an iron incorporated $sp^2$ carbon nanogranules (Fe/CNG) catalyst, the catalyst comprising (a) iron in the form of Fe(0), in bulk phase, (b) iron in the form of Fe(0) along with the $Fe_3C$ phase, and (c) trace amounts of Fe(II) and Fe(III), where (a), (b) and (c) are collectively present in the range from 5 to 20 w/w % of the sp2 carbon nanogranules, and wherein the trace amounts of Fe(ii) and Fe(III) are found on a surface of the sp2 carbon nanogranules, the process comprising the steps of:
   i. reducing the Fe/CNG catalyst under hydrogen or diluted hydrogen under pressure of atmospheric to 10 bar_g at a temperature in the range of 350 to 500° C. for a period in the range of 2 to 12 hours;
   ii. cooling the catalyst followed by heating under the flow of syngas and nitrogen with $H_2$ to CO mole ratio is in the range of 0.5:1 to 2:1 at GHSV of 2000 to 5000 $mLh^{-1}$ $g^{-1}$ at a temperature in the range of 300 to 380° C. under atmospheric pressure; and
   iii. pressurizing the bed at 5 to 30 bar to obtain lower olefins.

2. The process of claim 1, further comprising, prior to step (i):
   iv. dissolving heavy petroleum residue or vacuum residue in a solvent along with iron precursor to prepare a homogeneous solution;
   v. pumping the homogeneous solution as obtained in step (iv) at flow range of 0.5 mL/min to 5 mL/min to a quartz reactor tube placed in a furnace and spraying the solution to a reactor tube in presence of nitrogen flow in the range of 100 to 300 mL/min for a time period of 10 minute to 60 minutes to obtain carbon deposited on tube surface;
   vi. cooling the tube and collecting the carbon deposits from the surface as obtained in step (v.) of the reactor tube followed by washing with solvent to remove any unconverted residue; and
   vii. drying the carbon deposits as obtained in step (vi) and calcining at temperature in the range of 400 to 700° C. for a period in the range of 1 to 6 hours under nitrogen flow at 50 to 150 mL/min to obtain iron incorporated carbon nanogranules (Fe/CNG).

3. The process as claimed in claim 2, wherein the heavy petroleum residues used is vacuum residue from refinery consisting of polyaromatic hydrocarbons (PAH).

4. The process as claimed in claim 2, wherein the solvent used in step (iv or v) is an aromatic solvent selected from the group consisting of light naphtha, petroleum ether, benzene, toluene, xylene and ethylbenzene.

5. The process as claimed in claim 2, wherein the iron precursor used is an organometallic compound of iron.

6. The process as claimed in claim 2, wherein the iron precursor used is ferrocene.

7. The process as claimed in claim 2, wherein the weight composition of the heavy petroleum residue or vacuum residue used is in the range of 5 to 20%.

8. The process as claimed in claim 2, wherein weight composition of the iron precursor used is in the range of 5 to 20%.

9. The process as claimed in claim 1, wherein CO conversion efficiency is up to 30% and selectivity of light olefins is up to 50%.

10. The process as claimed in claim 1, wherein the light olefins from syngas obtained at lower rate of methanation of 15 to 17% and reduced conversion of CO to $CO_2$ at 12 to 15% with respect to the hydrocarbons.

* * * * *